United States Patent [19]

Dixit

[11] 4,346,298
[45] Aug. 24, 1982

[54] AUTOMATIC AIR PILLOW FOR DIAGNOSTIC X-RAY MACHINE

[76] Inventor: Jagannath K. Dixit, 1128 Sioux Dr., Crown Point, Ind. 46307

[21] Appl. No.: 239,674

[22] Filed: Mar. 2, 1981

[51] Int. Cl.³ .............................................. A61B 6/04
[52] U.S. Cl. ...................................... 5/441; 269/328; 378/208
[58] Field of Search .............. 250/439 R, 449; 5/441; 269/323, 328

[56] References Cited

U.S. PATENT DOCUMENTS

| | | | |
|---|---|---|---|
| 2,700,735 | 1/1955 | Kizaur | 250/449 |
| 3,595,223 | 7/1971 | Castagna | 269/328 |
| 3,795,021 | 4/1974 | Moniot | 5/441 |
| 3,915,153 | 10/1975 | Quinn | 250/439 |

Primary Examiner—Alfred E. Smith
Assistant Examiner—T. N. Grigsby
Attorney, Agent, or Firm—Howard I. Podell

[57] ABSTRACT

An automatic air pillow assembly for diagnostic X-ray machines adapted for mounting on a tiltable examination table having a compressor motor flowing air automatically through a three-way valve into an inflatable pillow. The valve is actuated by a mercury switch which senses the table position and allows flow into the pillow when the table is horizontal and cut when it is vertical. Various clamping means are provided to attach the pillow to different types of tables.

6 Claims, 6 Drawing Figures

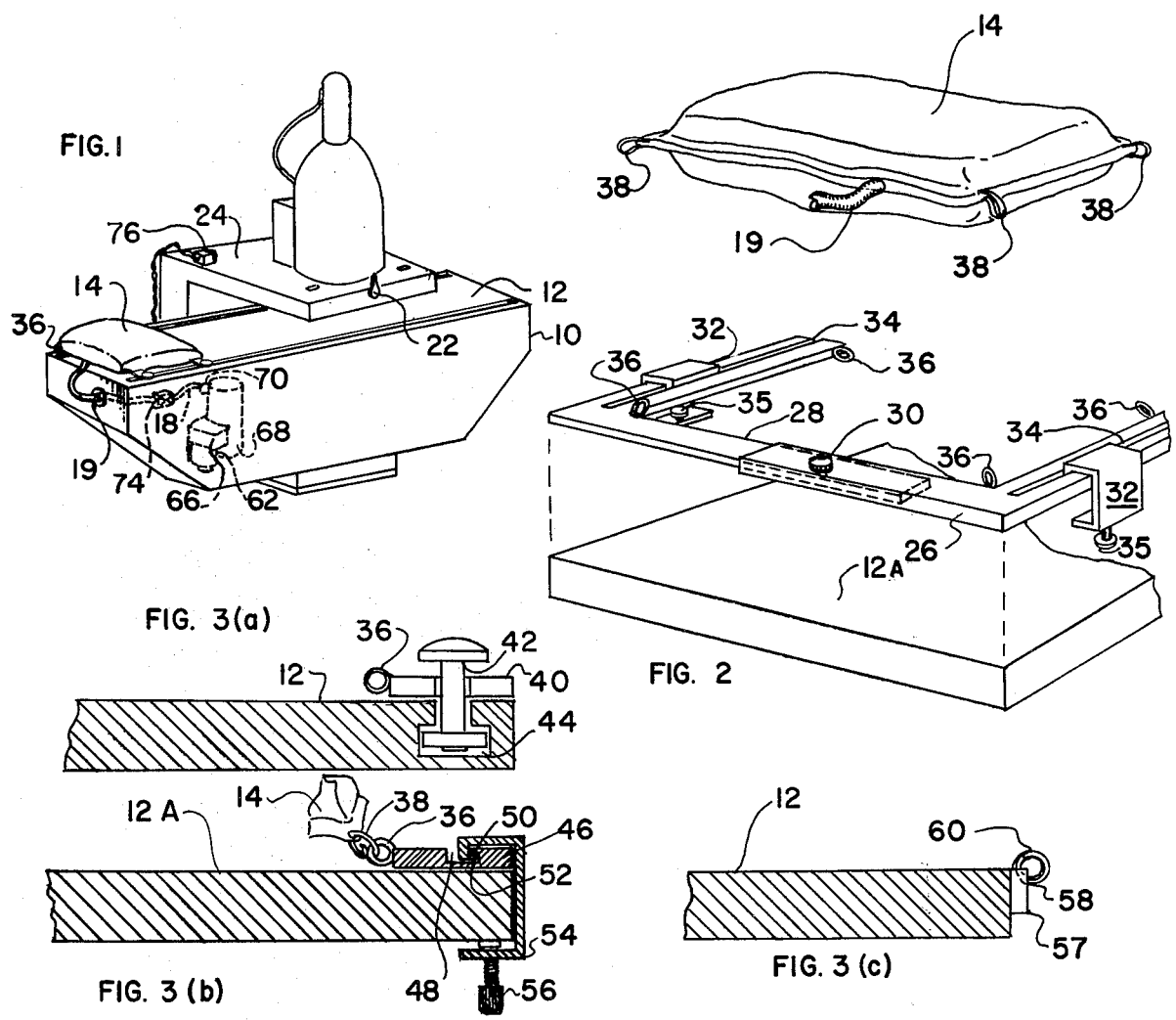
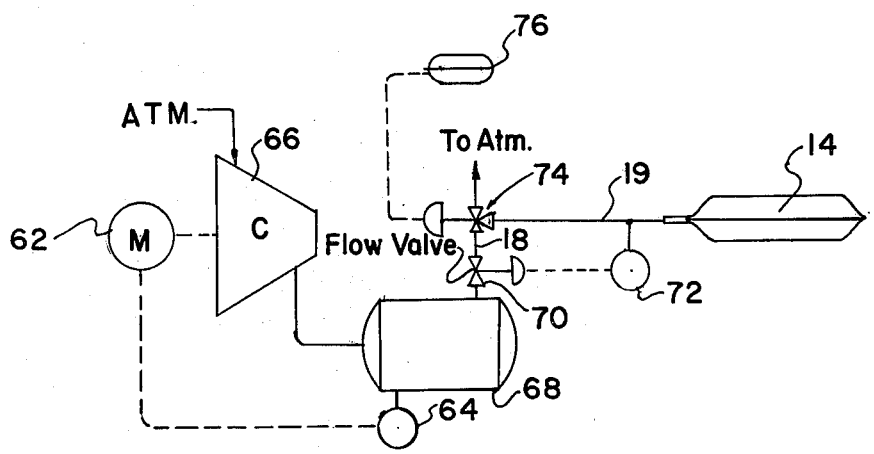

AUTOMATIC AIR PILLOW FOR DIAGNOSTIC X-RAY MACHINE

FIELD OF THE INVENTION

This invention relates generally to an automatic air pillow assembly for diagnostic fluoroscopic X-ray machines which I call "Dixie Flot". The assembly may be built in the X-ray machines or retrofitted thereto.

Fluoroscopic X-ray equipment is used for various examinations. Some of these fluoroscopic examinations (e.g. G.I. series, by far the most common examination) need to be done in a lying down as well as in a standing position. There are several different accessories at the fluoroscopic control such as moving table top, cones, shutters, boots for myelography and shoulder rests and remote control, which make the examination safe and comfortable for the patient and the examiner.

When the radiologist finishes the fluoroscopic examination in a standing position, the table is turned down in a horizontal position. The table is very hard and to add to the comfort of the patient a pillow is given by the technician so that the patient can rest comfortably as well as swallow the barium easily.

However, since the fluoroscopy is performed often in dark or semi-dark conditions finding a pillow and keeping it handy is difficult. Often patients push the pillow off the table during the examination and it has to be replaced several times. The technician often forgets to remove the pillow when the table is again moved into the standing position and then the pillow falls to the floor. Also if the remote control unit is used the assistant has to give and take the pillow off during the procedure.

The aim of this invention is to avoid this manipulation by using an air pillow which is simultaneously inflated or deflated when the table is in a horizontal or vertical position, respectively. This can be achieved in the following manner. When the table is turned down to the horizontal position, a position sensor switch device controls a three-way air valve to admit compressed air into the pillow from a source of compressed air, such as a pressure vessel, an air compressor or other air pump. When the table is turned up to a vertical position, the air rushes out of the pillow through the same three-way valve and the pillow collapses in an upright position.

The pillow can be fixed at the level of average height of a person at the head end of the table. If the patient is short, he can just slide up to the pillow when the table is made horizontal. Some fluoroscopic X-ray tables have gutters at the sides of the table tops where usually attachments like shoulder and head rests, foot rests, boots, or IVP compression bands are attached. Similarly, the pillow can slide up or down to the desired position in the gutters. Since the air pillow will have practically no weight even a very simple "Velcro" type material or simple hooks, etc., may be used to attach the pillow to the table with or without side gutter attachments so that the pillow can be attached or detached when needed.

DESCRIPTION OF THE PRIOR ART

The prior art, as exemplified by U.S. Pat. Nos. 3,828,377; 3,905,591; 3,873,841; 3,783,863; 2,639,206; 3,851,644; 4,030,719; 3,823,709; and 3,806,110 is generally illustrative of the pertinent art but the aforementioned patents are non-applicable to the present invention. While the prior art expedients are generally acceptable for their intended purposes only, they have not proven entirely satisfactory in that they are either complex and expensive to manufacture, or bulky and inconvenient to use, or require unusual skill and/or dexterity to operate. As a result of the shortcomings of the prior art, typified by the above, there has developed a substantial need for improvement in this field.

The principal object of this invention is to provide a device or article of this character which combines simplicity, strength and durability in a high degree, together with inexpensiveness of construction owing to the minimum of parts so as to encourage widespread use thereof.

Additional objects and advantages of the invention will be set forth in part in the description which follows in part will be obvious from the description, or may be realized by practice of the invention, the objects and advantages being realized and attained by means of the instrumentalities and combinations particularly pointed out in the appended claims.

BRIEF DESCRIPTION OF THE DRAWING

In the accompanying drawing, in which is shown one of the various possible illustrative embodiments of this invention, wherein like reference character identify the same or like parts:

FIG. 1 is an isometric view of an examination table equipped with an inflatable pillow in accordance with this invention;

FIG. 2 is a partial, exploded view of a width and adjustable mounting assembly;

FIG. 3A is a partial sectional view of mounting means to a table having side gutters;

FIG. 3B is the same for a solid table;

FIG. 3C is the same for another type of mounting; and

FIG. 4 is a schematic representation of the assembly.

DESCRIPTION OF THE PREFERRED EMBODIMENTS

With reference to the drawing, there is shown and illustrated an inflatable pillow assembly constructed in accordance with the principles of the invention and designated generally by reference character 10. The illustrated tangible embodiment of the invention includes an examination table 10 of the tip or tiltable type which has an upper surface 12 for the reception of a patient. Motor means are provided in such tables whereby the same can be made to assume positions in upwardly or downwardly spaced relations to the floor on which the table 10 rests in response to manual actuation of switch 22. Exemplary of such tables are those described in U.S. Pat. Nos. 2,639,206 and 3,334,951.

Viewed in its simplest form in FIG. 1, the invention includes an inflatable standard size rubber pillow fitted with a machine washable, decorative pillow case. The pillow 14 is connected via three-way valve 74 and tube 18 to an accumulator or pressure vessel 68 containing enough compressed air to inflate the pillow several times. Valve 74 is a three-way valve which allows air from the accumulator to fill the pillow when the table is moved to a horizontal position. A mercury switch 76 fixed to the table controls operation of valve 74. The preferred location of the mercury switch 76 is on the fluoroscopic control area 24 of the table.

Various attaching means are provided for securing pillow 14 to table top 12, or a table top 12A that projects beyond the table 10.

Thus, FIG. 2 shows a width adjustable frame composed of two interfitting U-shaped members 26, 28 clamped together by screw 30. Sliding clamps 32 are mounted in side grooves 34 in the members 26, 28. Clamps 32 include on the lower part thereof a clamping screw 35 which engages the underside of table top 12A; rings 36 are fixed at each corner of the frame and receive straps 38 on each corner of the pillow 14.

FIG. 3A shows part of a frame 40 which has a slider 42 engaged in side gutter 44 of table top 12.

FIG. 3B shows attaching means similar to that shown in FIG. 2 for table tops 12A without side gutters and consisting of a U-shaped metal frame 46 having a groove 48 with lateral projection 50 engaged by the hook part 52 of side clamp 54 whose lower part is threaded with a clamp screw 56 bearing on the underside of table top 12A.

FIG. 3C shows other attaching means consisting of metal plates 57 with hole 58 with a key ring 60 to which the straps 38 are attached. The plates are magnetic or glued to the side of table 10. Instead of plates 57 with hole 58, holes for attachment of ring 60 may be drilled into the sides of table top 12.

FIG. 4 shows in block form the preferred embodiment of the invention. A compressor motor 62 controlled by pressure sensitive switch 64 forces air from the atmosphere into compressor 66 and accumulator 68. A flow valve 70 is controlled by pressure switch 72 located on the inlet tube 19 to pillow 14, with flow valve 70 mounted on the outlet leading from the accumulator 68 to tube 18 that leads to the three-way valve 74. Three-way directional control valve 74 is controlled by position sensitive mercury switch 76 to which fills pillow 14 in the horizontal position of the table or to allow it to deflate when the table 12 is vertical.

The three positions of the valve are helpful. For example, when the table moves from the horizontal to the vertical position, the mercury switch is set so that the pillow does not start deflation unless the table passes to the position of more than forty-five degrees tilt. Also when the table is moved from the upright vertical to the horizontal positioning the inflation does not start unless the table is tilted beyond this position of forty-five degrees tilt. This is advantageous as initially the inflation of the pillow is not needed.

The details of the valves, the mercury position switch and the pressure vessel can be obtained from any compressed air equipment manufacturer of equiment which is suitable for this purpose.

The elements above described can be mounted inside table 10 or secured to one side thereof.

The operation and use of the invention hereinabove described will be evident to those skilled in the art to which it relates from a consideration of the foregoing.

The present invention is believed to accomplish among others all of the objects and advantages herein set forth.

Without further analyses, the foregoing will so fully reveal the gist of this invention that those skilled in the art can by applying current knowledge thereto readily adapt it for various applications without omitting certain features which can constitute essential characteristics of the generic or specific aspects of this invention. Therefore, a more lengthy description is deemed unnecessary.

It is intended that various changes may be made in this invention in the practical development thereof, if desired. Such changes are comprehended within the meaning and range of equivalency of the following claims. The invention, therefore, is not to be restricted except as is necessitated by the prior art.

Having thus described the invention, what is claimed as new and to be secured by Letters Patent is:

1. An inflatable pillow assembly for use in connection with an examination table of the tip type having a table surface and having motor means for rotating said table between horizontal and vertical positions and switch means for actuating said motor:
   an inflatable pillow,
   a source of compressed air; a three-way valve connecting said pillow to said source; said valve including a vent outlet; said valve being actuated by said switch means whereby said pillow is inflated when said table is brought to said horizontal position and is deflated when said table is brought to said vertical position; and support means for detachably securing said pillow to said table.

2. The invention as recited in claim 1, wherein said support means include a width adjustable frame and clamps slidably mounted on said frame for securing same to said table.

3. The invention as recited in claim 1, wherein said table has side gutters and said support means comprises a U-shaped frame; fasteners connecting said frame to said gutters and rings on said frame for attaching said pillow thereto.

4. The invention as recited in claim 1, wherein said support means consist of a plurality of plates fixed on the sides of said table; rings on said plates and means for attaching said pillow to said rings.

5. The invention as recited in claim 1, further including a motor for actuating said compressor and an accumulator receiving air therefrom.

6. The invention recited in claim 1, wherein said support means comprises ring fasteners attachable to the table through holes in the side of the top of said table; which ring fasteners are attachable to said pillow.

* * * * *